(12) United States Patent
Martin

(10) Patent No.: US 9,468,477 B2
(45) Date of Patent: Oct. 18, 2016

(54) FLEXIBLE BONE SCREW

(71) Applicant: Daniel L. Martin, Palo Alto, CA (US)

(72) Inventor: Daniel L. Martin, Palo Alto, CA (US)

(73) Assignee: Syntorr, Inc., Palo Alto, CA (US)

( * ) Notice: Subject to any disclaimer, the term of this patent is extended or adjusted under 35 U.S.C. 154(b) by 12 days.

(21) Appl. No.: 14/462,494

(22) Filed: Aug. 18, 2014

(65) Prior Publication Data

US 2014/0371747 A1 Dec. 18, 2014

Related U.S. Application Data

(62) Division of application No. 11/951,282, filed on Dec. 5, 2007, now Pat. No. 8,808,338.

(51) Int. Cl.
*A61B 17/72* (2006.01)
*A61B 17/68* (2006.01)
*A61B 17/17* (2006.01)
*A61B 17/86* (2006.01)

(52) U.S. Cl.
CPC ....... *A61B 17/7208* (2013.01); *A61B 17/1717* (2013.01); *A61B 17/1728* (2013.01); *A61B 17/68* (2013.01); *A61B 17/8605* (2013.01); *A61B 17/8625* (2013.01); *A61B 17/8635* (2013.01); *A61B 17/7233* (2013.01); *A61B 17/8645* (2013.01); *A61B 2017/1778* (2013.01)

(58) Field of Classification Search
CPC .......................... A61B 17/7208; A61B 17/68
See application file for complete search history.

(56) References Cited

U.S. PATENT DOCUMENTS

| | | | | |
|---|---|---|---|---|
| 3,118,444 | A | * | 1/1964 | Serrato, Jr. ........ A61B 17/7208 606/104 |
| 3,842,824 | A | | 10/1974 | Neufeld |
| 3,892,232 | A | * | 7/1975 | Neufeld ............... A61B 17/742 606/104 |
| 4,312,337 | A | * | 1/1982 | Donohue ........... A61B 17/1796 606/103 |
| 4,483,335 | A | * | 11/1984 | Tornier .............. A61B 17/7208 606/64 |

(Continued)

FOREIGN PATENT DOCUMENTS

| | | |
|---|---|---|
| FR | 2844701 A1 | 3/2004 |
| JP | 2003-010199 A | 1/2003 |

(Continued)

OTHER PUBLICATIONS

European Office Action dated Nov. 7, 2011 in counterpart European Patent Application 08 858 591.1-2310.

(Continued)

*Primary Examiner* — Christian Sevilla
(74) *Attorney, Agent, or Firm* — Patterson & Sheridan, LLP

(57) ABSTRACT

A flexible bone screw for insertion into the intramedullary cavity of a fractured bone facilitates enduring fixation of the fracture. The flexible bone screw includes a substantially smooth shaft and a threaded portion positioned at one end of the shaft, wherein the outer diameter of the threaded portion is greater than the shaft diameter and the length of the threaded portion is about 20% of the overall length of the flexible bone screw or less.

20 Claims, 17 Drawing Sheets

(56) References Cited

U.S. PATENT DOCUMENTS

| | | | |
|---|---|---|---|
| 4,640,271 A | | 2/1987 | Lower |
| 4,712,541 A | * | 12/1987 | Harder ................. A61B 17/921 606/67 |
| 4,940,467 A | | 7/1990 | Tronzo |
| 4,978,350 A | | 12/1990 | Wagenknecht |
| 5,312,255 A | | 5/1994 | Bauer |
| 5,709,687 A | * | 1/1998 | Pennig ................... A61B 17/80 411/368 |
| 5,814,047 A | | 9/1998 | Emilio et al. |
| 6,030,162 A | * | 2/2000 | Huebner ............ A61B 17/1682 411/263 |
| 6,270,499 B1 | | 8/2001 | Leu et al. |
| 6,309,396 B1 | * | 10/2001 | Ritland .............. A61B 17/1717 606/80 |
| 6,419,678 B1 | * | 7/2002 | Asfora ............... A61B 17/1757 606/96 |
| 6,524,313 B1 | | 2/2003 | Fassier et al. |
| 6,533,788 B1 | * | 3/2003 | Orbay ................ A61B 17/7208 606/62 |
| 6,558,386 B1 | | 5/2003 | Cragg |
| 6,660,009 B1 | * | 12/2003 | Azar .................... A61B 17/921 606/232 |
| 6,926,718 B1 | | 8/2005 | Michelson |
| 6,949,100 B1 | | 9/2005 | Venturini |
| 8,679,120 B2 | * | 3/2014 | Frigg ................. A61B 17/1717 606/62 |
| 2002/0111629 A1 | * | 8/2002 | Phillips .............. A61B 17/7208 606/62 |
| 2003/0187446 A1 | | 10/2003 | Overaker et al. |
| 2005/0273107 A1 | | 12/2005 | Stevens |
| 2006/0149263 A1 | | 7/2006 | Newcomb et al. |
| 2006/0173291 A1 | * | 8/2006 | Glossop ................. A61B 19/52 600/424 |
| 2006/0195099 A1 | * | 8/2006 | Bottlang ............ A61B 17/8605 606/67 |
| 2006/0219661 A1 | | 10/2006 | Towse et al. |
| 2007/0173834 A1 | * | 7/2007 | Thakkar .............. A61B 17/7208 606/62 |
| 2009/0043337 A1 | * | 2/2009 | Martin ............... A61B 17/0401 606/232 |
| 2009/0149890 A1 | * | 6/2009 | Martin ............... A61B 17/1717 606/316 |
| 2009/0306718 A1 | * | 12/2009 | Tipirneni ............... A61B 17/92 606/263 |
| 2012/0191134 A1 | * | 7/2012 | Martin ............... A61B 17/0401 606/232 |

FOREIGN PATENT DOCUMENTS

| | | |
|---|---|---|
| WO | 9851241 A1 | 11/1998 |
| WO | 2005096976 A1 | 10/2005 |

OTHER PUBLICATIONS

Extended European Search Report, PCT/US2008/085139, dated Apr. 27, 2011.

"Kirschner Wires" <http://www.rfq.de/eng/kirschner_eng.htm>. 1995-2007. pp. 1-5.

"Kirshner Wires and Steinmann Pins" <http://www.mede.de/english/k-wire/index.htm>. 2005. pp. 1-2.

"Kirschner Wire" <http://en.wikipedia.org/wiki/Kirschner_wire>. 2007. pp. 1-2.

"Traumatology and General Osteosynthesis" www.Synthes.com <http://www.Synthes.com> 2006. 8 pgs.

Eaberg, et al. "Percutaneous Stabilization of Unstable Francutes of the Humerus." The Journal of Bone and Joint Surgery. 1992. pp. 508-515.

Jakob, et al. "Four-Part Valgus Impacted Fractures of the Proximal Humerus." From Inselspital, Berne. vol. 73-B, No. 2 , Mar. 1991. pp. 295-298.

Defranco, et al. "Evaluation and Management of Valgus Impacted Four-Part Proximal Humerus Fractures." Clinical Orthopaedics and Related Research. 2006. pp. 109-114.

Williams, et al. "Two-Part and Three-Part Fractures." Open Reduction and Internal Fixation Versus Closed Reduction and Percutaneous Pinning. vol. 31, No. 1. Jan. 2000. 23 pgs.

Resch, et al. :Percutaneous Fixation of Three- and Four-Part Fractures of the Proximal Humerus. From the General Hospital of Salzburg and the University Hospital of Innsbruck, Austria. vol. 79-B, No. 2 Mar. 1997. pp. 295-300.

Keener, et al. "Outcomes after percutaneous reduction and fixation of proximal humeral fractures." vol. 16, No. 3. May/Jun. 2007. pp. 330-338.

Williams, et al. "Percutaneous Pinning of Humerus Fractures." Surgeons Cite Challenges of Percutaneous Pinning for Proximal Humeral Fractures. ORTHOSuperSite.com. May 2007. 4 pgs.

Sythes. www.Synthes.com <http://www.Synthes.com>. Traumatology and General Osteosynthesis. 2006. Catalog 10, p. 45, Catalog 10, p. 44. 4 pgs.

International Search Report dated Apr. 20, 2009.

* cited by examiner

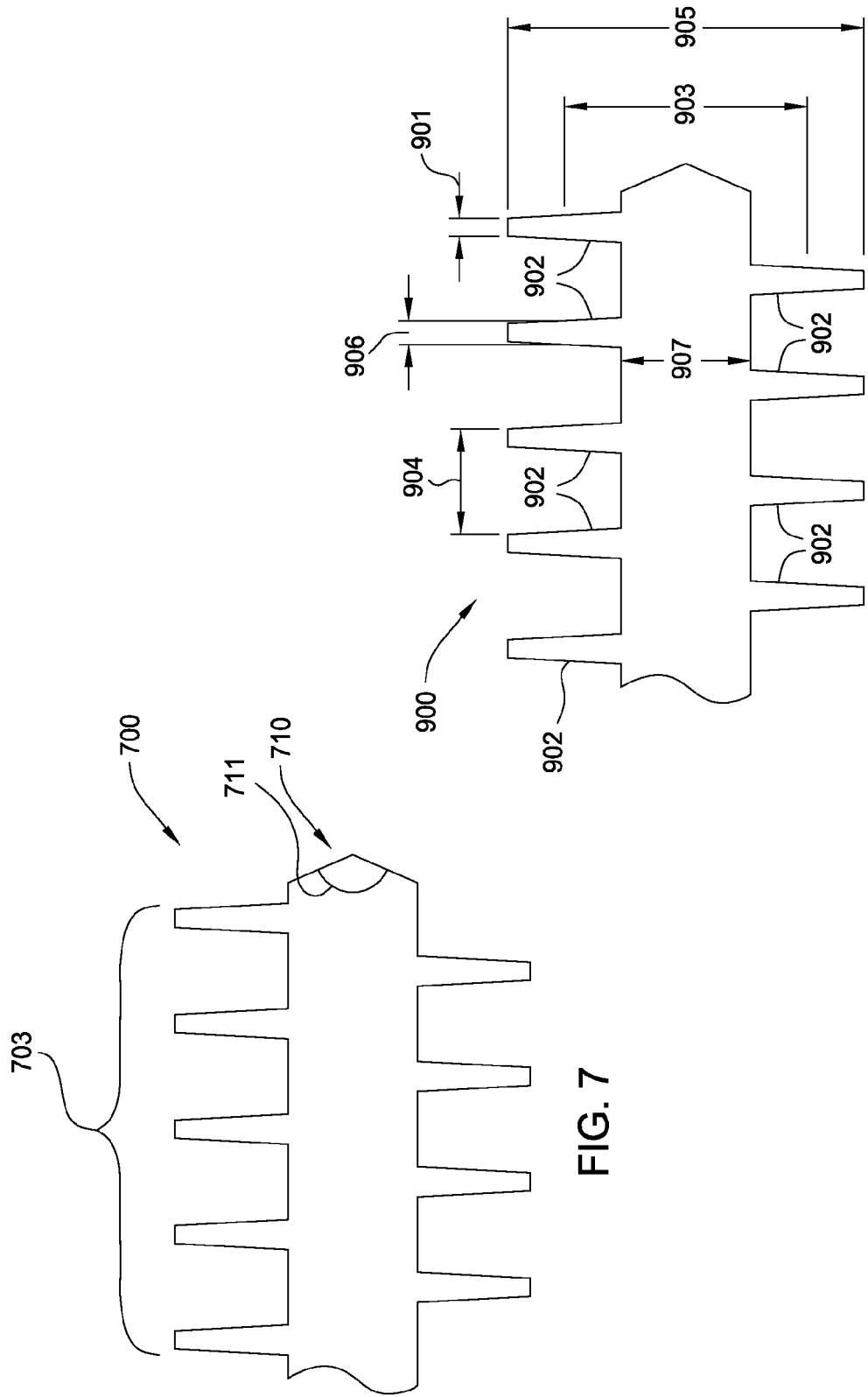

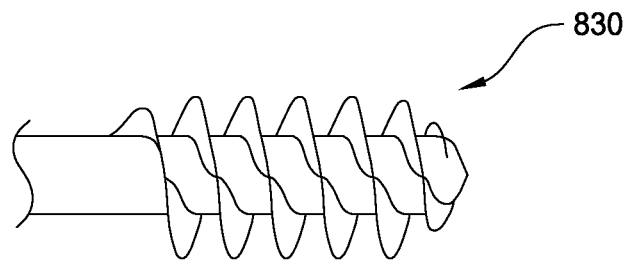
FIG. 8E
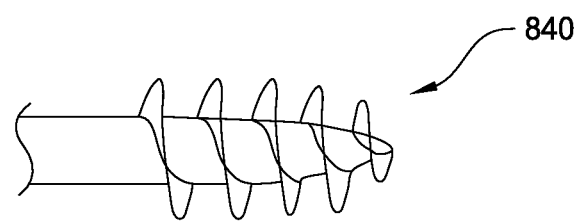
FIG. 8F
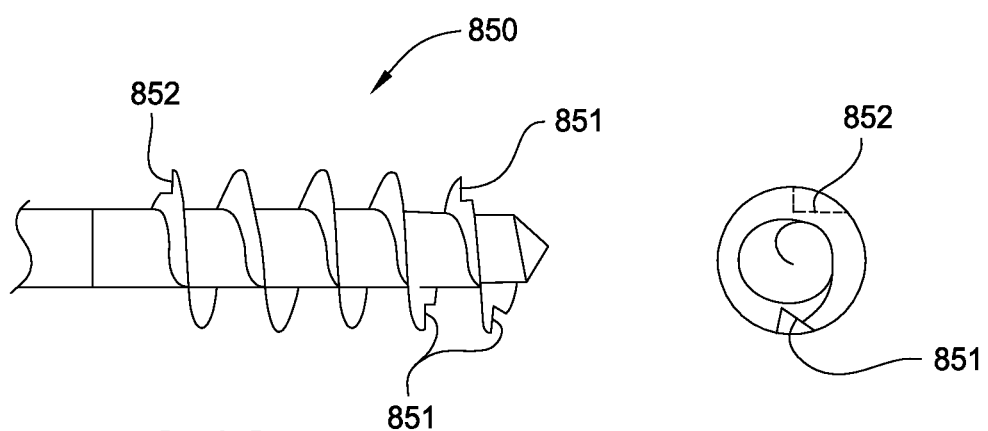
FIG. 8G
FIG. 8H

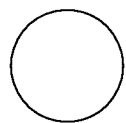 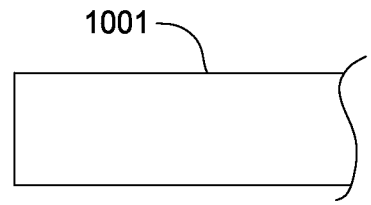
FIG. 10A
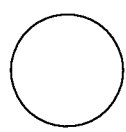 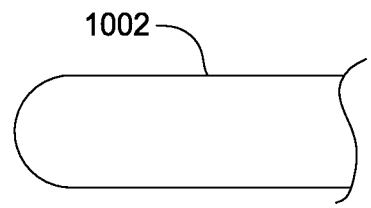
FIG. 10B
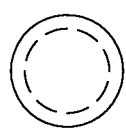 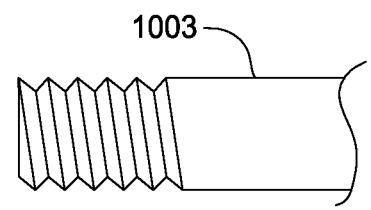
FIG. 10C
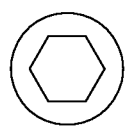 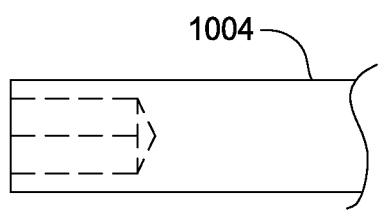
FIG. 10D
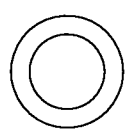 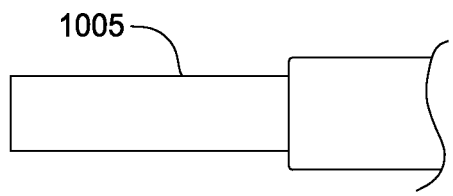
FIG. 10E
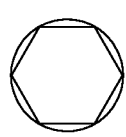 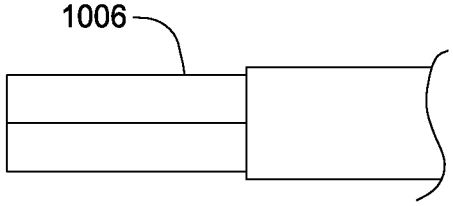
FIG. 10F

FLEXIBLE BONE SCREW

CROSS-REFERENCE TO RELATED APPLICATIONS

This application is a divisional of U.S. patent application Ser. No. 11/951,282, filed on Dec. 5, 2007, entitled "FLEXIBLE BONE SCREW", the entire contents of which are incorporated herein by reference.

BACKGROUND OF THE INVENTION

1. Field of the Invention

Embodiments of the present invention relate generally to orthopedic surgery and, more particularly, to bone screws for management of bone fractures.

2. Description of the Related Art

Surgical techniques for the treatment of bone fractures commonly known and used in the art include external fixation, pinning, and joint replacement. In some situations, each of these techniques can be inadequate for facilitating satisfactory recover of the bone fracture.

A proximal humerus fracture, i.e., a fracture of the humerus near the humeral head, is one such case. Replacement of the shoulder joint with a prosthesis is a complex and invasive procedure that can lead to the death of elderly patients, for whom proximal humerus fractures are common. External fixation of a proximal humerus fracture with one or more humeral plates and bone screws may successfully maintain the correct position of the humerus fragments, but the extensive dissection of soft tissue that is an integral part of this approach leads to high morbidity.

As illustrated in FIG. 1A, rigid, threaded-tip pins 101 may be used for percutaneous fixation of a humeral head 102 of a humerus 100 to bone shaft 103 to treat a proximal humerus fracture 120. Threaded-tip pins 101 are inserted through cortex 105 and into subchondral bone 106 of humeral head 102. In elderly patients who have suffered a proximal humerus fracture, bone of humeral head 102 is generally porous and soft and tends to collapse subsequent to fracture reduction and pinning. The collapse tends to occur adjacent to fracture 120, where the bone is also most fragmented. Further, the soft bone of humeral head 102 does not hold the tips of threaded-tip pins 101 securely. Because threaded-tip pins 101 are held in place at a single point that is relatively far from subchondral bone 106, i.e., penetration point 104 of cortex 105, threaded-tip pins 101 are free to angulate or tilt about penetration point 104 and therefore offer little stability to humeral head 102. Collapse or fragmentation of the bone of humeral head 102 and poor fixation of threaded-tip pins 101 in subchondral bone 106 allow further movement between humeral head 102 and bone shaft 103. A displacement force is applied by muscles to bone shaft 103, further causing movement at fracture 120. Tilting of threaded-tip pins 101 allows humeral head 102 to be angulated and displaced from bone shaft 103, as illustrated in FIG. 1B. Such angulation and displacement require additional surgery for satisfactory recovery of proximal humerus fracture 120.

FIG. 2A illustrates another prior art method for percutaneous fixation of the humeral head 202 of a humerus 200 to a bone shaft 203 to treat a proximal humerus fracture 230. First, humeral head 202 is returned to its proper position on bone shaft 203, using methods standard to the art of orthopedic surgery. Then, one or more fully-threaded K-wires 201 are introduced into the intramedullary cavity 210 of humerus 200 through an opening 204 in the antero-lateral cortex 205 of humerus 200. For clarity, only one fully-threaded K-wire 201 is depicted in FIG. 2A. Fully-threaded K-wires 201 are then advanced into the intramedullary cavity 210, along far cortex 207, and threaded into the subchondral bone 206. Because each fully threaded K-wire 201 is supported by far cortex 207 and is not free to angulate or tilt, humeral head 202 is not subject to angulation or displacement if subchondral bone 206 collapses after fixation or if fixation of K-wire 201 in humeral head 202 is suboptimal. However, collapse of humeral head 202 does produce other complications when the method illustrated in FIG. 2A is used to fixate proximal humeral fracture 230.

FIG. 2B illustrates humerus 200 after fixation with one or more fully-threaded K-wires 201. As shown, collapse of bone adjacent to fracture 230 results in penetration of the shoulder joint by fully threaded k-wire 201. This is because the threads on the shaft of fully threaded K-wire 201 engage the edges of opening 204 and hold fully threaded K-wire 201 in place as bone adjacent to fracture 230 collapses. Even if opening 204 is over-sized relative to the outer diameter of fully threaded K-wire 201, the threads on the shaft of fully threaded K-wire 201 engage the edge of opening 204 due to loading caused by the elastic bend in fully threaded K-wire 201. In addition, fully threaded K-wire 201 has limited holding power in the relatively soft material of subchondral bone 206, since fully threaded K-wire 201 must have a relatively small diameter in order to have the necessary flexibility for insertion into humerus 200. The limited holding power of fully threaded K-wire 201 further encourages penetration of the joint as bone adjacent to fracture 230 collapses. Joint penetration by fully threaded K-wire 201 can lead to unwanted cartilage and bone damage and requires immobilization of the joint for the duration of treatment, i.e., until proximal humeral fracture 230 has healed and fully threaded K-wire 201 has been removed.

An additional complication associated with the approach illustrated in FIG. 2A is K-wire breakage. Some small diameter models of fully threaded K-wires known in the art have sufficient flexibility for use as fully threaded K-wire 201 as described above. However, it is known that the bending moment exerted on fully threaded K-wire 201 when rotationally inserted into humerus 200 can result in breakage of fully threaded K-wire 201 in the intramedullary cavity 210, which is highly undesirable. This breakage is related to the notch effect of the threads on the shaft of K-wire 201. Rotation of the elastically bent K-wire 201 during insertion causes cyclic loading that accentuates the notch effect.

A further complication of K-wire usage is the penetration of far cortex 207. If the tips are too sharp, i.e., the included angle of the point is too small, K-wire 201 tends to penetrate far cortex 207 rather than slide or rotationally advance along the inner surface of far cortex 207 as it is rotationally inserted. This problem is especially notable for trocar point K-wires. A further reason for penetration of far cortex 207 is that there is lacking instrumentation and methodology which can direct the K-wires away from entry into far cortex 207.

Accordingly, there is a need in the art for devices and methods for the management of bone fractures which prevent angulation and displacement of bone fragments, do not result in joint penetration by repair devices due to collapse of bone of the head, avoid breakage of repair devices inside the fractured bone, and avoid penetration of the far cortex by repair devices during their insertion.

SUMMARY OF THE INVENTION

The present invention provides devices and methods used in repairing bone fractures. According to one embodiment of the invention, a flexible bone screw comprises a shaft and a threaded portion at one end of the shaft, where the threaded portion has an outer diameter that is larger than the shaft diameter and a length that is 20% of the length of the flexible bone screw or less, and the ratio of the length of the flexible bone screw to the shaft diameter is at least 50.

According to another embodiment of the invention, a flexible bone screw comprises a first end including a tool engagement portion, a second end including a threaded portion, and a shaft between the first end and the second end. In this embodiment, the tool engagement portion has a diameter that is substantially the same or less than the shaft diameter, which is 3 mm or less, and the threaded portion has an outer diameter that is larger than the shaft diameter and a length that is 20% of the length of the flexible bone screw or less.

According to another embodiment of the invention, a method for repairing a bone fracture comprises the steps of inserting a flexible bone screw retrograde into a curved screw guide, inserting the curved screw guide having the flexible bone screw resting therein into an intramedullary cavity of the bone, rotating the flexible bone screw to connect the flexible bone screw to a portion of the bone, and removing the curved screw guide from the intramedullary cavity after connecting the flexible bone screw to the portion of the bone.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 7 illustrates a partial cross-sectional view of a flexible bone screw having a threaded portion, where the tip of the threaded portion has an included angle that is at least 80°, according to an embodiment of the invention.

FIGS. 8A-H illustrate drill tips that may be incorporated into a flexible bone screw, according to embodiments of the invention.

FIG. 9 illustrates a cross-sectional view of a threaded portion of a flexible bone screw, according to embodiments of the invention.

FIGS. 10A-F illustrate tool engagement portions that may be incorporated into a flexible bone screw, according to embodiments of the invention.

For clarity, identical reference numbers have been used, where applicable, to designate identical elements that are common between figures. It is contemplated that features of one embodiment may be incorporated in other embodiments without further recitation.

DETAILED DESCRIPTION

Embodiments of the invention contemplate a flexible bone screw for insertion into the intramedullary cavity of a fractured bone to facilitate reduction and/or fixation of the fracture. Embodiments further provide a method of flexible bone screw insertion into the intramedullary cavity of a fractured bone. The flexible bone screw according to embodiments of the invention prevents angulation and displacement between bone fragments, reduces the risk of bone screw breakage, avoids joint penetration by the bone screw, and avoids penetration of the bony cortex opposite the entry hole.

Figure 1B:
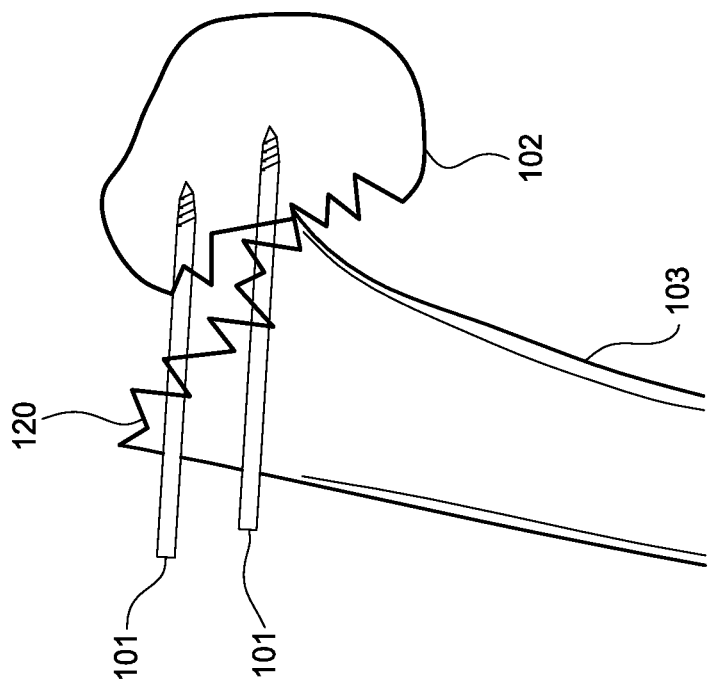
FIGS. 1A and 1B illustrate threaded-tip pins used for percutaneous fixation of a humeral head of a humerus to bone shaft to treat a proximal humerus fracture.
Figure 1A:
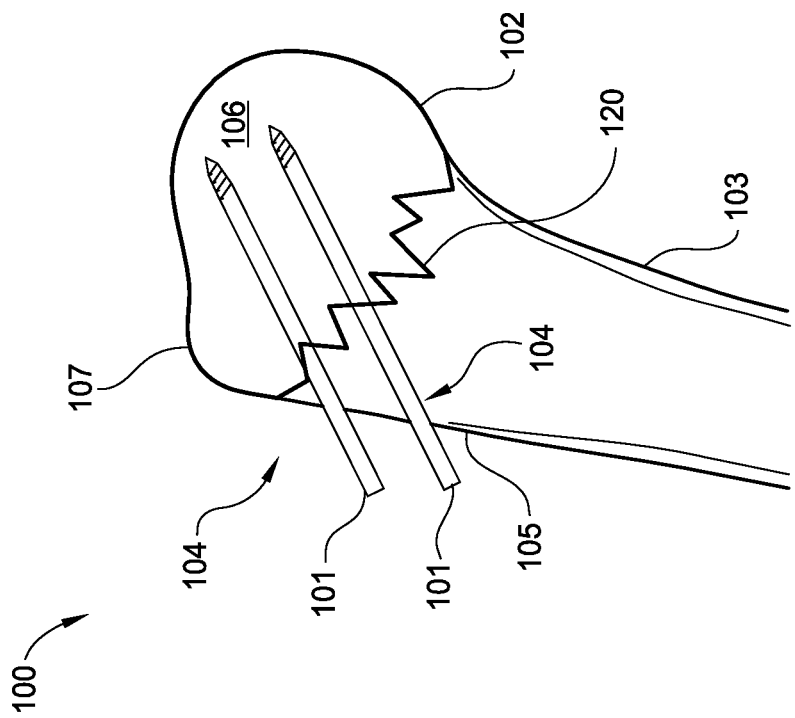
Figure 2A:
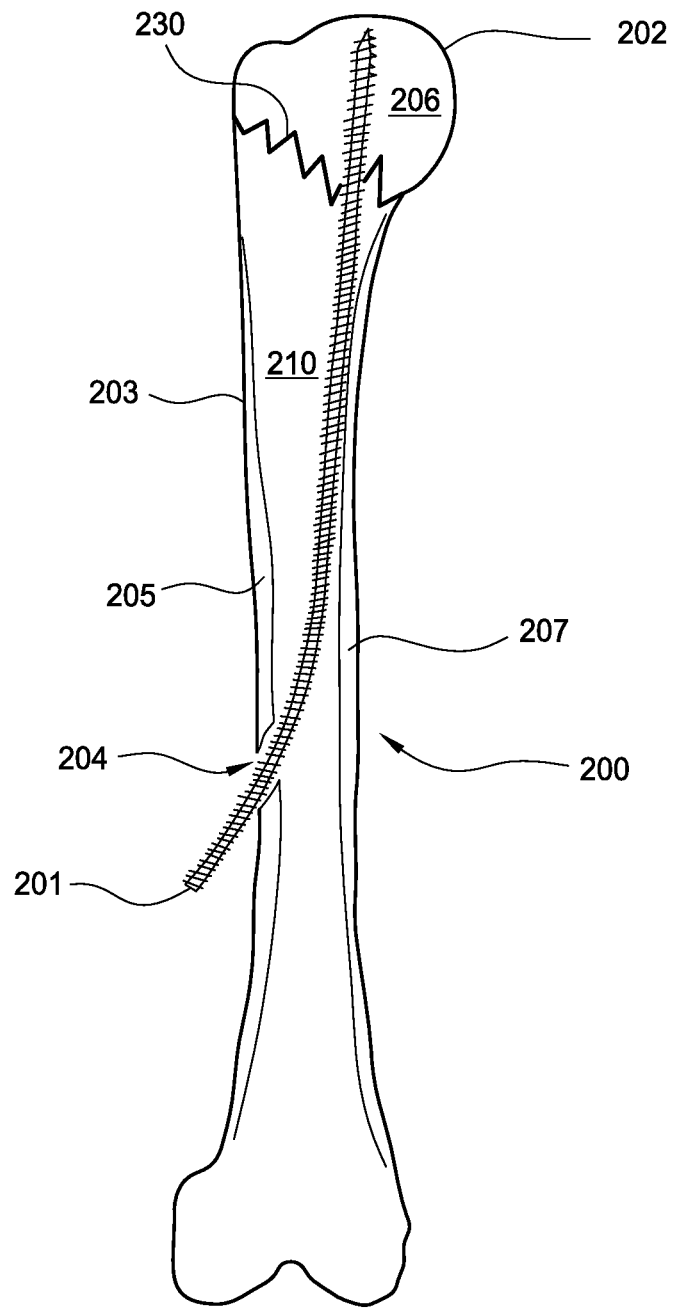
FIGS. 2A and 2B illustrate percutaneous fixation of the humeral head with one or more fully-threaded K-wires to treat a proximal humerus fracture.
Figure 2B:
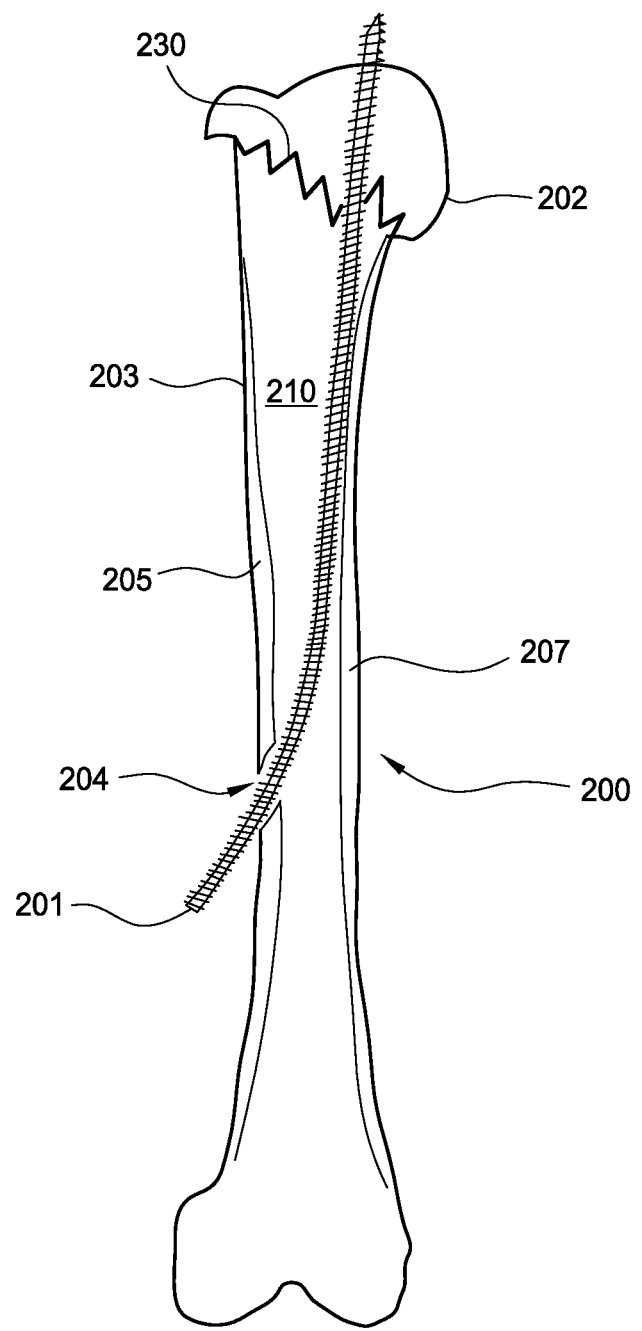
Figure 3:
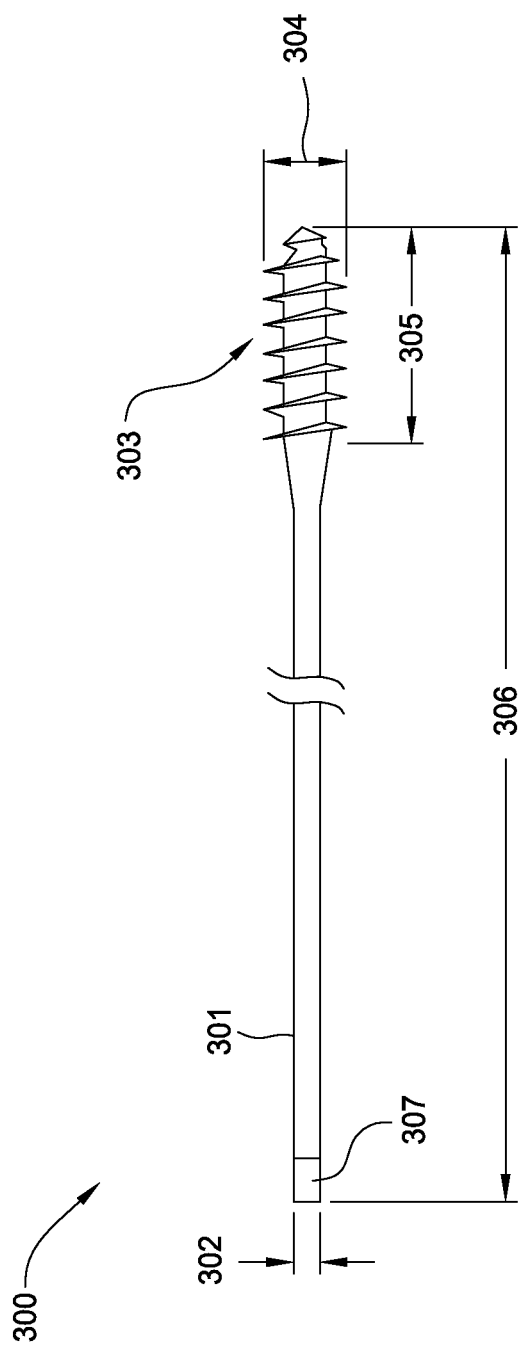
FIG. 3 depicts a flexible bone screw configured for percutaneous management of proximal humerus fractures, according to one embodiment of the invention.

FIG. 3 depicts a flexible bone screw 300 configured for management of proximal humerus fractures, e.g., percutaneous management of proximal humerus fractures, according to one embodiment of the invention. Flexible bone screw 300 is fabricated from stainless steel and includes a shaft 301 with a shaft diameter 302 and a threaded portion 303. The surface of shaft 301 is substantially smooth, having a surface roughness, Ra, of less than about 3 micrometers, where the surface roughness is measured parallel to the axis of shaft 301. The smooth shaft surface allows easy gliding of shaft 301 into the entry hole, so that if the head should collapse, shaft 301 slides out of the entry hole rather than being engaged with the entry hole, which would force threaded portion 303 through subchondral bone with prior art devices. Threaded portion 303 is positioned at one end of shaft 301 for engagement with bone material, has a length 305, and has an outer diameter 304 that is larger than shaft diameter 302. A tool engagement portion 307 is positioned at the opposite end of shaft 301 to facilitate attachment of flexible bone screw 300 to a manual or powered screw-rotating device (e.g., element 420 in FIG. 4A) and does not engage against bone. Flexible bone screw is configured so that tool engagement portion 307 and any extra length of shaft 301 can be cut off at the completion of surgery. In this embodiment, shaft diameter 302 is between 1.7 mm and 3 mm; overall length 306 is at least 200 mm, preferably 300 mm; length 305 is between 6 mm and 25 mm, and outer diameter 304 is between 3 mm and 5 mm. Having a shaft diameter less than 3 mm allows a shaft stiffness which is not excessive for manipulation by the surgeon during surgery. In order for flexible bone screw 300 to have the necessary flexibility as contemplated by the inventor, i.e., an elastic bending arc of at least 15°, the ratio of length 306 to shaft diameter 302 is at least about 50:1. It is preferred that the elastic bending arc be at least 30° and the ratio of length 306 to shaft diameter 302 be at least about 100:1. This avoids use of the screw substantially in the plastic bending range to an extent that would cause mechanical failure of the screw. The elastic bending arc of a flexible bone screw is described below in conjunction with FIG. 5. Tool engagement portion 307 has a length that is less than one-tenth of length 306.

Other embodiments are contemplated, where one or more features of flexible bone screw 300, as described above, may have different dimensions based on what bone is being treated, the location of the fracture, and other factors. For example, the ratio of length 305 to overall length 306 may be as high as 0.20, the ratio of outer diameter 304 to shaft diameter 302 may vary between about 1.2 and about 4.0, and the possible elastic bending arc may be greater than 15°. Other features that may have different values include shaft diameter 302, outer diameter 304, length 305, and overall length 306. In addition, the material may be a titanium-based alloy, such as Ti 6-4, which would allow the use of higher possible shaft diameter while maintaining the flexibility to attain an elastic bending arc of 15° or greater.

Figure 4A:
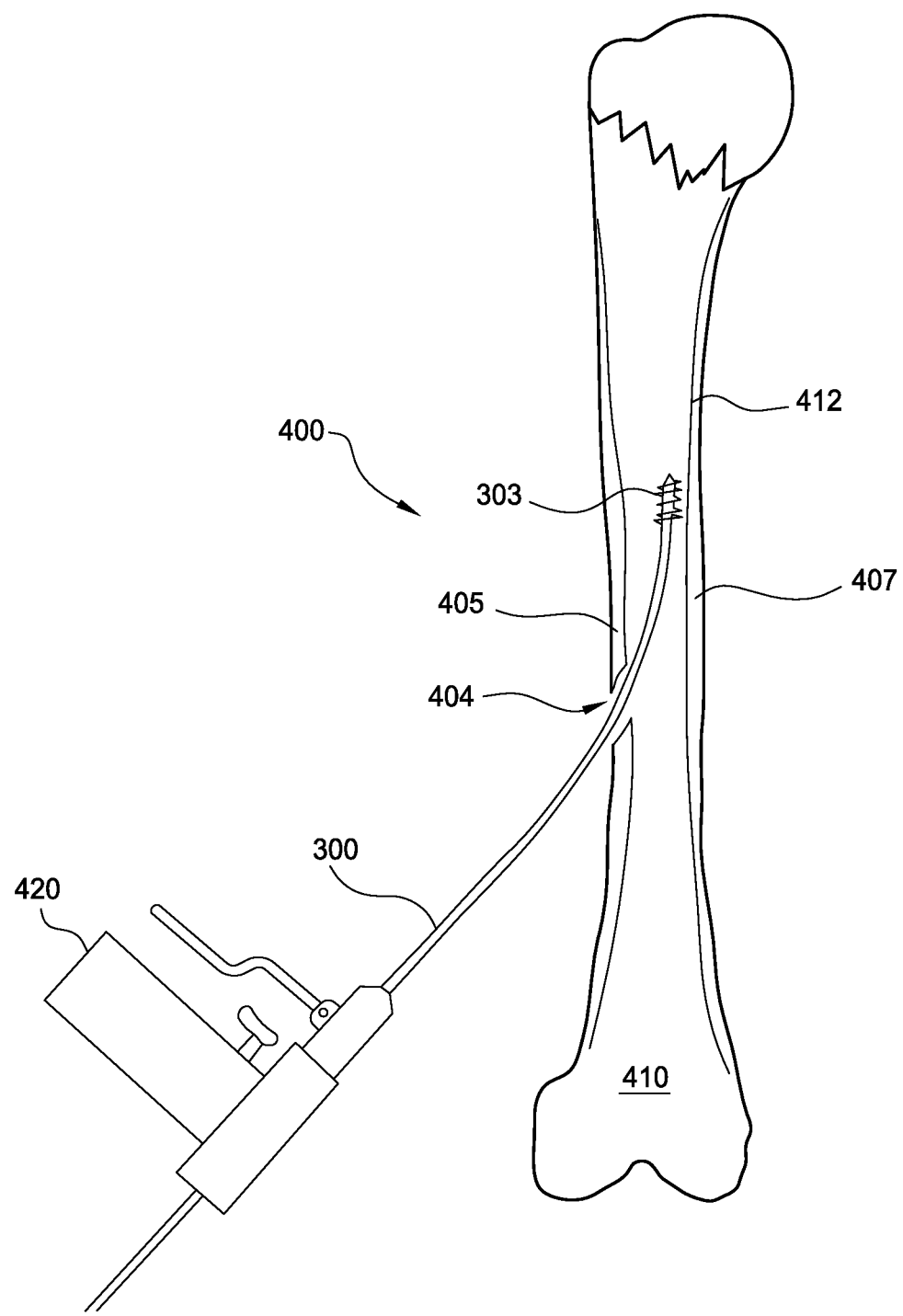
FIGS. 4A and 4B illustrate a flexible bone screw inserted obliquely into an antero-lateral opening in a cortex of a humerus.

In operation, as illustrated in FIG. 4A, flexible bone screw 300 is inserted obliquely into an antero-lateral opening 404 in a cortex 405 of a humerus 400. In this embodiment, a powered screw-rotating device 420 is coupled to the tool engagement portion of flexible bone screw 300 to rotate flexible bone screw 300 as the screw is inserted into the intramedullary cavity 410 of humerus 400. Because flexible bone screw 300 contacts far cortex 407 at an oblique angle, e.g., less than about 40°, and because flexible bone screw 300 is configured to be flexible enough to attain a substantially elastic bending arc of greater than 15° and the tip has an included angle of greater than 80°, the tip of threaded portion 303 does not penetrate far cortex 407 and instead is deflected off inner surface 412 of far cortex 407.

Figure 4B:
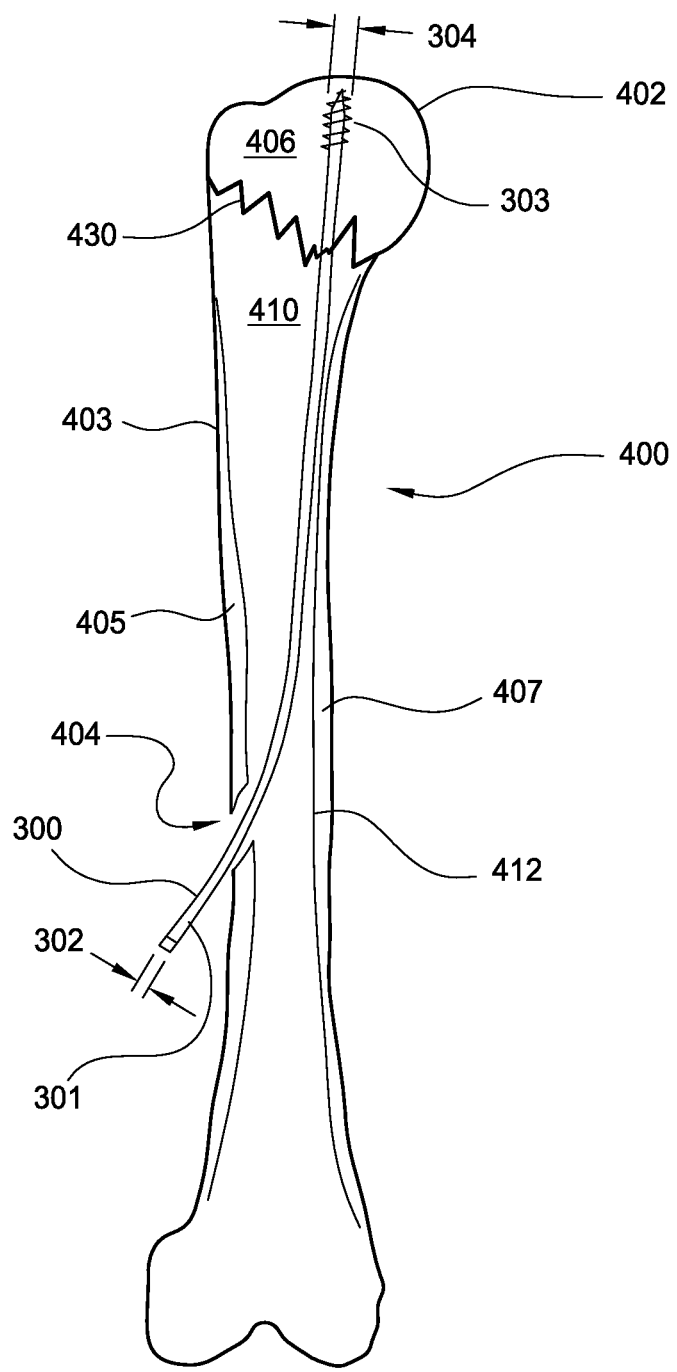

Referring to FIG. 4B, flexible bone screw 300 is further advanced into intramedullary cavity 410 after deflecting off inner surface 412 of far cortex 407 until threaded portion 303 is engaged with subchondral bone 406. In this way, flexible bone screw 300 is positioned in a distal-to-proximal ("retrograde" in orthopedic parlance) orientation, i.e., substantially parallel to the major axis of humerus 400, so that humeral head 402 is not subject to angulation and displacement after fixation of proximal humerus fracture 430 if bone adjacent to fracture 430 collapses. In the event of bone collapse, flexible bone screw 300 is free to slide back out of antero-lateral opening 404, since shaft 301 of flexible bone screw 300 is substantially smooth, thereby preventing joint penetration by flexible bone screw 300. In addition, because outer diameter 304 of threaded portion 303 is larger than shaft diameter 302, flexible bone screw 300 has more holding power in subchondral bone 406 than the holding power of the fully threaded K-wire used in the prior art, which has an outer diameter equal to shaft diameter 302. The improved holding power of threaded portion 303 secures proximal humerus fracture 430 in place and suppresses joint penetration by flexible bone screw 300 due to bone collapse. Additionally, the shaft 301 is less susceptible to breakage during advancement since it is substantially smooth and does not include threads. The smooth surface of shaft 301 also facilitates removal from humerus 400.

Figure 5:
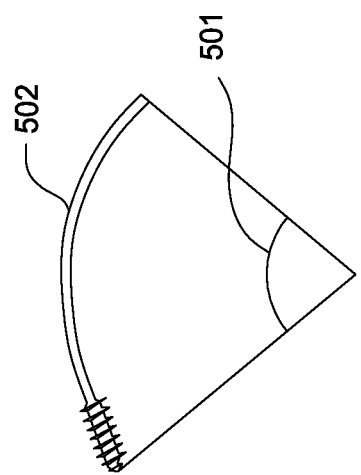
FIG. 5 illustrates the elastic bending arc of a flexible bone screw.

FIG. 5 illustrates the elastic bending arc 501 of a flexible bone screw 502, where flexible bone screw 502 represents flexible bone screw 300 described in FIG. 3. Elastic bending arc 501 is defined as the maximum arc of curvature, in degrees, that can be produced by flexible bone screw 502 without flexible bone screw 502 undergoing substantial plastic deformation. Hence, a more flexible bone screw has an elastic bending arc of greater degree than a less flexible bone screw. The elastic bending arc of the flexible bone screws according to the embodiments of the invention is by design much greater than any other prior art bone screws made of the same metal, and this characteristic addresses specific previously unsolved needs in fracture treatment, and this characteristic has been achieved by carefully adjusting the dimensions in a way that is not observed in the prior art. The achievement of the special dimensions requires special and difficult manufacturing techniques not previously seen in the field of the invention, techniques which would not be developed if the dimensions did not offer unique, novel advantages, as has been demonstrated by the inventor.

One reason for the importance of the ratio of the length 306 to shaft diameter 302 and bending arc 501 is that they largely define how easily the bone screw may be manipulated by the surgeon. The surgeon must be able to bend the bone screw to a minimum arc of 15°, and preferably to an arc of 30°, without the use of excessive force or localized glove pressure, in order to insert the bone screw with hand held tools. For larger shaft diameters, the surgeon obtains greater bending leverage by having a correspondingly longer bone screw length 306, but the elastic bending arc, in such a case, would remain the same. The inventor has determined that, for the humerus bone and stainless steel screws, preserving manipulability by preserving elastic bending arc is valid up to shaft diameter 302 of about 3 mm. Other metal alloys with lower elastic modulus allow slightly greater shaft diameter 302.

Figure 6:
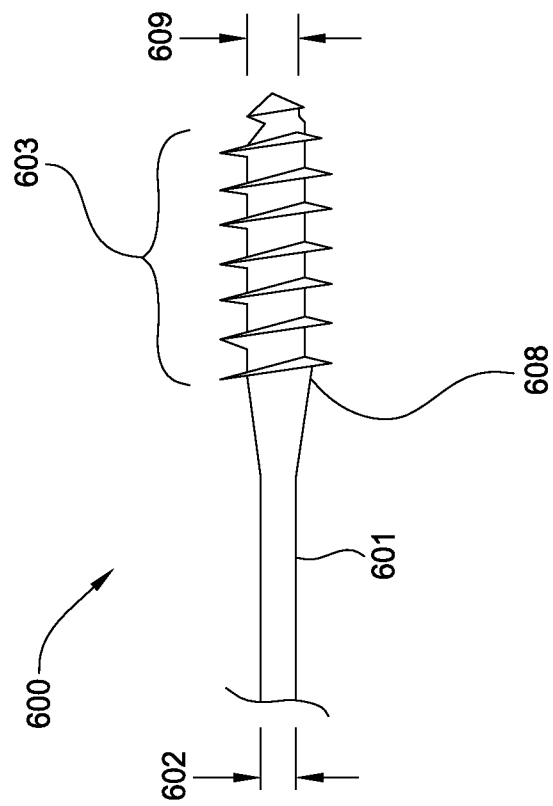
FIG. 6 illustrates a partial schematic view of a flexible bone screw having a tapered portion joining a shaft and a threaded portion, according to one embodiment of the invention.

FIG. 6 illustrates a partial schematic view of a flexible bone screw 600 having a tapered portion 608 joining a shaft 601 and a threaded portion 603, according to one embodiment of the invention. In this embodiment, threaded portion 603 has an inner diameter 609 that is larger than shaft diameter 602. The inventor has determined that when inner diameter 609 of threaded portion 603 is larger than shaft diameter 602, breakage in the location where shaft 601 joins threaded portion 603 is avoided.

FIG. 7 illustrates a partial cross-sectional view of a flexible bone screw 700 having a threaded portion 703, where the tip 710 of threaded portion 703 has an included angle 711 that is at least 80°, according to an embodiment of the invention. In this embodiment, tip 710 of flexible bone screw 700 is optimized to improve the performance of flexible bone screw 700 when flexible bone screw 700 first contacts an internal surface of the humerus cortex. To minimize the potential for penetration of the far cortex of a bone, for example far cortex 407 of humerus 400, illustrated in FIGS. 4A and 4B, the tip of threaded portion 703 of flexible bone screw 700 is designed to have an included angle of at least 80°. The inventor has determined that when tip 710 contacts a surface at a non-normal angle and included angle 711 is substantially less than 80°, tip 710 may still penetrate the surface, rather than being deflected. Hence, as flexible bone screw 700 is inserted obliquely into the intramedullary cavity of a fractured bone and included angle 711 is at least about 80°, flexible bone screw 700 glances off the inner surface of the far cortex.

The inventor has also determined that the tip configuration of a flexible bone screw may be optimized to improve the penetration and holding power of the bone screw when the bone screw engages subchondral bone material. In different situations, it is contemplated that a spade tip, trocar tip, threaded tip, or a corkscrew tip may be beneficially incorporated into a flexible bone screw for improved performance.

Figure 8A:
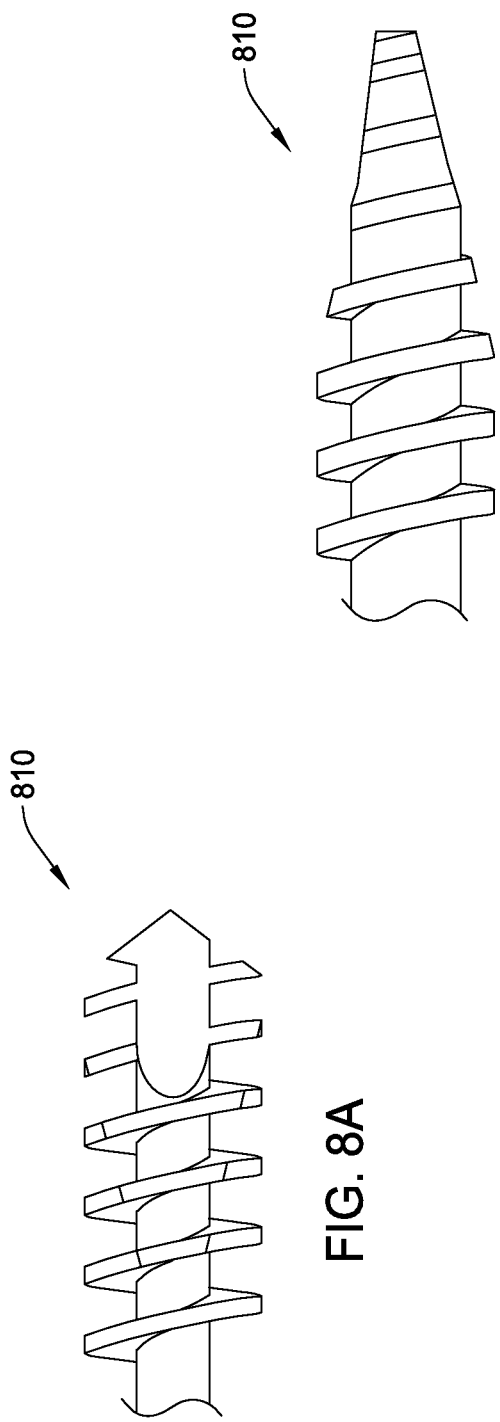
Figure 8B:
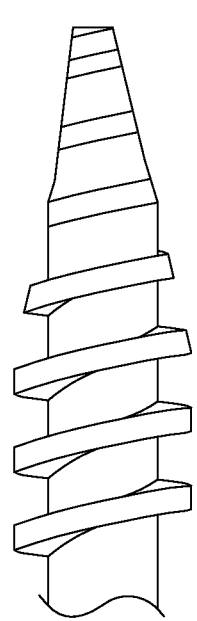
Figure 8C:
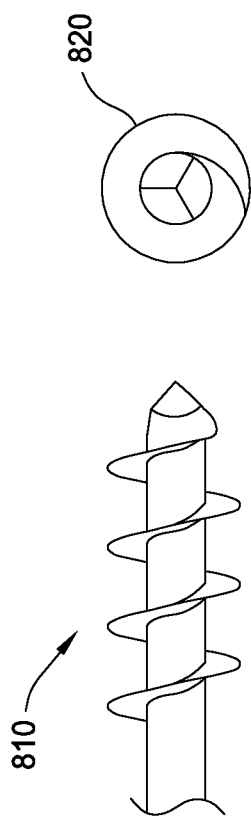
Figure 8D:
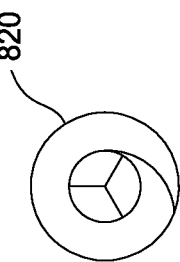

FIG. 8A illustrates a side view of a spade tip 810 that may be incorporated into a flexible bone screw, according to an embodiment of the invention. FIG. 8B illustrates a 90-degree rotated view of spade tip 810. FIG. 8C illustrates a partial side view of a trocar tip 820 that may be incorporated into a flexible bone screw, according to an embodiment of the invention. FIG. 8D illustrates a head-on view of trocar tip 820. FIG. 8E illustrates a side view of a threaded tip 830 that may be incorporated into a flexible bone screw, according to an embodiment of the invention. In the embodiment depicted in FIG. 8E, threaded tip screw 830 is a double lead threaded screw tip; however, other varieties of threaded tips are also contemplated as part of a flexible bone screw. FIG. 8F illustrates a partial side view of a corkscrew tip 840 that may be incorporated into a flexible bone screw, according to an embodiment of the invention. As shown, corkscrew tip 840 has a tapered core tip, where the core may end before the tip of the screw. FIG. 8G illustrates a side view of a fluted screw tip 850 having forward cutting flutes 851 and a reverse cutting flute 852. FIG. 8H illustrates a head-on view of fluted screw tip 850. Forward cutting flutes 851 and reverse cutting flute 852 facilitate the penetration of fluted screw tip 850 into subchondral or other bone material during bone fragment fixation, and the reverse cutting flutes facilitate subsequent removal after fracture healing. In addition, the penetration efficiency of a flexible bone screw may be enhanced by configuring the outer diameter of the threaded portion of the bone screw to be smaller at the tip of the threaded portion, according to one embodiment of the invention. Examples of this embodiment are illustrated in FIGS. 8E and 8F.

The inventor has also determined that the thread configuration of the threaded portion of a flexible bone screw may be optimized to improve the holding power of the bone screw in subchondral or other relatively soft bone material by maximizing the surface area of each thread in contact with surrounding bone tissue and minimizing displacement of bone volume. It is contemplated that a number of factors related to thread configuration may be so optimized, including thread width relative to thread diameter, and the ratio of thread pitch to thread outer diameter. FIG. 9 illustrates a cross-sectional view of a threaded portion 900 of a flexible bone screw, according to embodiments of the invention. Thread pitch diameter is defined as the sum of thread outer diameter 905 plus core diameter 907, divided by two. Holding power of threaded portion 900 is improved when thread width 901 of threads 902 at thread pitch diameter 903 is less than one half of thread pitch 904. Holding power of threaded portion 900 is also improved when the ratio of thread pitch 904 to outer thread diameter 905 is greater than about 0.2 and less than about 0.5.

It is contemplated that the tool engagement portion of a flexible bone screw may have various configurations, including straight-ended, rounded, threaded, a hex recess with increased diameter, reduced diameter, and flat-sided. FIG. 10A illustrates an end-on view and a partial side view of a straight-ended tool engagement portion 1001 that may be incorporated into a flexible bone screw, according to an embodiment of the invention. FIG. 10B illustrates an end-on view and a partial side view of a rounded tool engagement portion 1002 that may be incorporated into a flexible bone screw, according to an embodiment of the invention. Rounded tool engagement portion 1002 serves to prevent puncture of a surgeon's glove during surgery, and to aid in retrograde insertion of a flexible bone screw into a curved screw guide, which is described below in conjunction with FIG. 11. FIG. 10C illustrates an end-on view and a partial side view of a threaded tool engagement portion 1003 that may be incorporated into a flexible bone screw, according to an embodiment of the invention. The threaded portion of threaded tool engagement portion 1003 engages in an internally threaded portion of a standard surgical insertion tool. FIG. 10D illustrates an end-on view and a partial side view of a tool engagement portion 1004 having a hex recess that may be incorporated into a flexible bone screw, according to an embodiment of the invention. FIG. 10E illustrates an end-on view and a partial side view of a tool engagement portion 1005 having a reduced diameter that may be incorporated into a flexible bone screw, serving to engage a standard K-wire driving tool (e.g., tool 420 shown in FIG. 4A) which will not accommodate the full diameter of the shaft, according to an embodiment of the invention. FIG. 10F illustrates an end-on view and a partial side view of a tool engagement portion 1006 with multiple flat sides that may be incorporated into a flexible bone screw, according to an embodiment of the invention for accommodation within the jaws of a standard surgical drill chuck.

Figure 11:
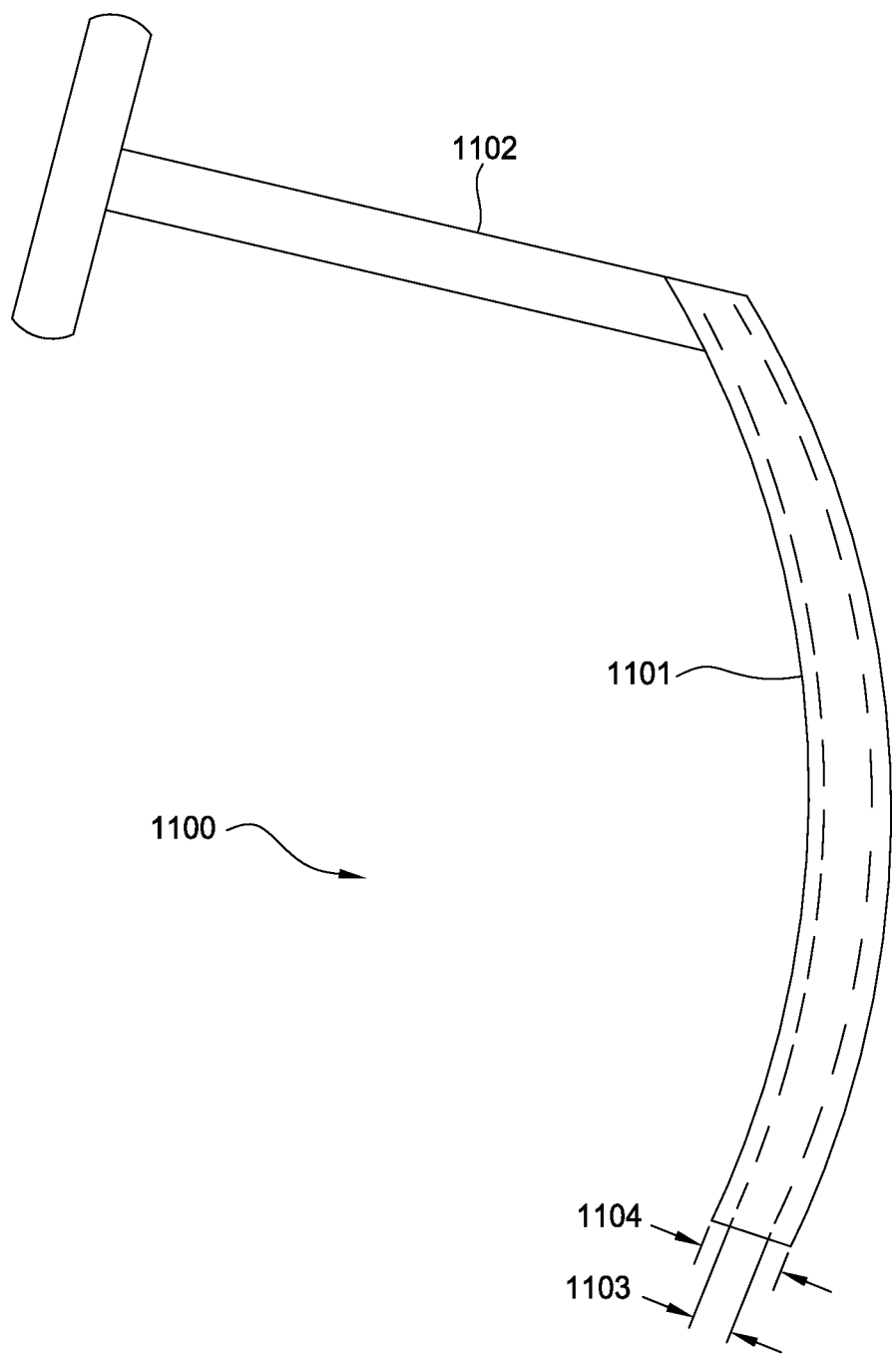
FIG. 11 schematically illustrates a curved screw guide, according to an embodiment of the invention.

Embodiments of the invention further contemplate a curved screw guide configured to facilitate the insertion of a flexible bone screw as described herein, such as flexible bone screw 300, into the intramedullary cavity of a fractured bone. FIG. 11 schematically illustrates a curved screw guide 1100, according to an embodiment of the invention. Curved screw guide 1100 may be constructed of stainless steel or other durable surgical-grade material, such as titanium and titanium-containing alloys. Curved screw guide 1100 includes a curved tube 1101 and a holding means 1102, such as a T-handle or other grip. Inner diameter 1103 of curved tube 1101 is selected so that the shaft of a flexible bone screw as described herein may be inserted into curved tube 1101 in a retrograde manner, i.e., inserted in the opposite direction that curved tube 1101 is inserted into the intramedullary cavity. Inner diameter 1103 is selected to be smaller than the outer diameter of the threaded portion of the flexible bone screw, so that the threaded portion remains outside curved tube 1101 without sliding into curved tube 1101 in the retrograde direction, and outer diameter 1104 is selected to be smaller than the outer diameter of the threaded portion of the flexible bone screw, so that entry into the bone hole is not hindered by the curved screw guide 1100. In one embodiment, inner diameter 1103 is approximately 10% to 100% larger than the shaft diameter of a flexible bone screw inserted therein. Curved screw guide 1100 is configured so that a flexible bone screw may be guided into the intramedullary cavity of a fractured bone, and oriented appropriately to engage the humeral head or other desired bone fragment when the bone screw is advanced into the fractured bone. Curved screw guide 1100 is also configured to minimize the risk of the flexible bone screw penetrating the far cortex of the fractured bone by providing a means for directing the flexible bone screw as required within the intramedullary cavity. The minimum radius of curvature of curved screw guide 1100 varies depending on the shaft diameter and the material of the flexible bone screw being inserted. In one embodiment of a stainless steel screw, the minimum radius of curvature of the curved screw guide 1100 is no less than 90 times the shaft diameter of the flexible bone screw. The inventor has determined that the approximate minimum radius of curvature for stainless steel is 90*d where d is the shaft diameter. Alloys with higher elastic limit, such as titanium alloys, allow a radius of curvature less than 90*d. Thus, if the minimum radius of curvature of the curved screw guide 1100 is no less than 90 times the shaft diameter of the flexible bone screw, substantial plastic deformation of the flexible bone screw inserted into the curved screw guide 1100 is avoided. It is understood that the curved screw guide 1100 can be constructed to have a portion which is tangent to a portion which is curved and that the radii of curvature of the curved screw guide 1100 can vary at different positions along the length thereof.

Figure 12A:
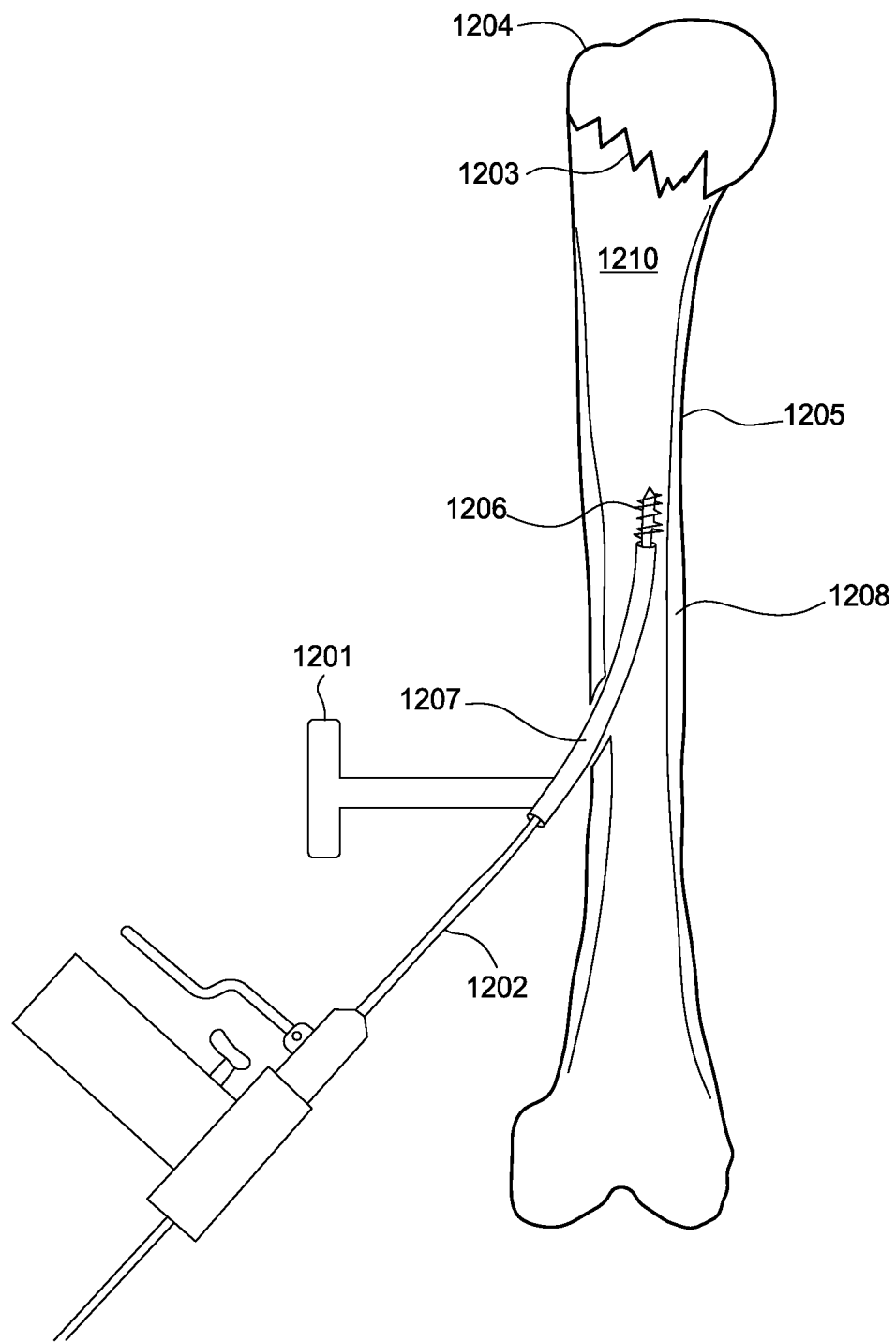
FIGS. 12A and 12B illustrate a curved screw guide with a flexible bone screw positioned therein.
Figure 12B:
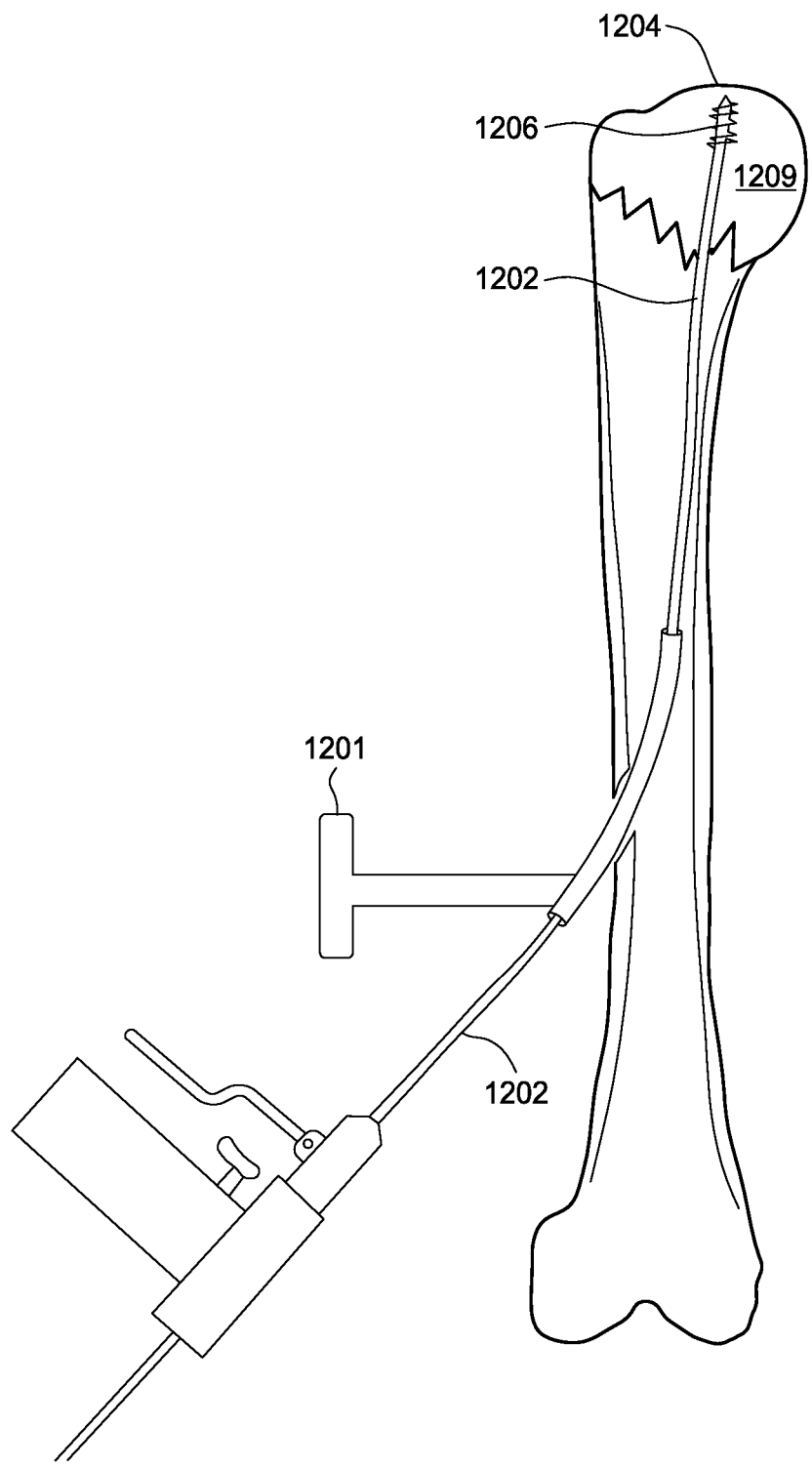

FIG. 12A illustrates a curved screw guide 1201 with a flexible bone screw 1202 positioned therein after insertion into the intramedullary cavity 1210 of a humerus 1205 and prior to advancement of flexible bone screw 1202 across a fracture 1203 and into the humeral head 1204. As shown, threaded portion 1206 is not contained in curved tube 1207 of curved screw guide 1201, and is oriented toward humeral head 1204 with reduced contact against far cortex 1208. FIG. 12B illustrates curved screw guide 1201 with flexible bone screw 1202 therein, after engagement of threaded portion 1206 with the subchondral bone 1209 of humeral head 1204.

Figure 13:
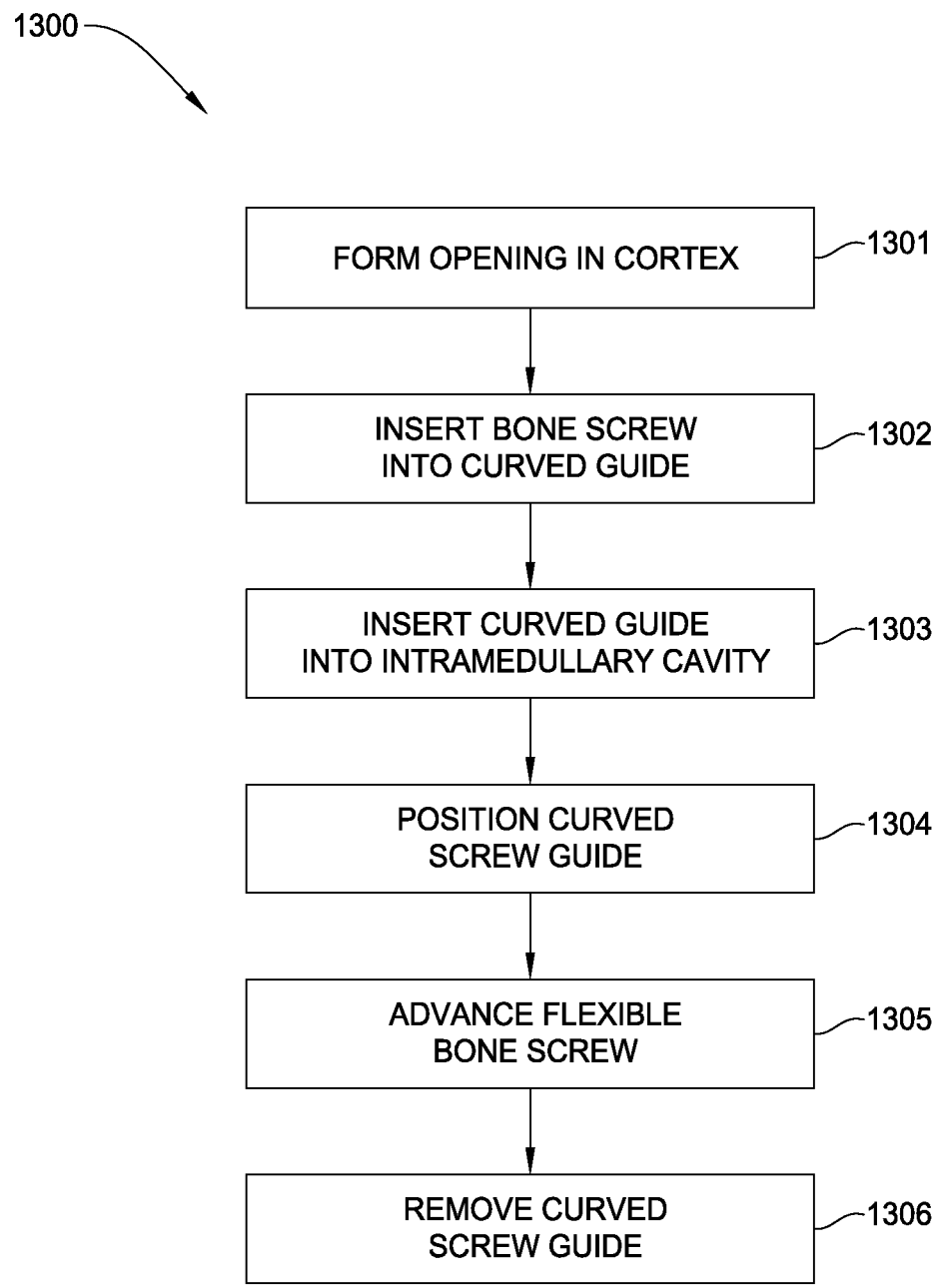
FIG. 13 is a flow chart summarizing a sequence of steps for repairing a bone fracture using a flexible bone screw and curved screw guide, according to an embodiment of the invention.

FIG. 13 is a flow chart summarizing a sequence of steps 1300 for repairing a bone fracture using a flexible bone screw and curved screw guide, according to an embodiment of the invention. In this embodiment, a proximal humerus fracture is repaired, although it is contemplated that other fractures may be treated in a similar manner.

Figure 14:
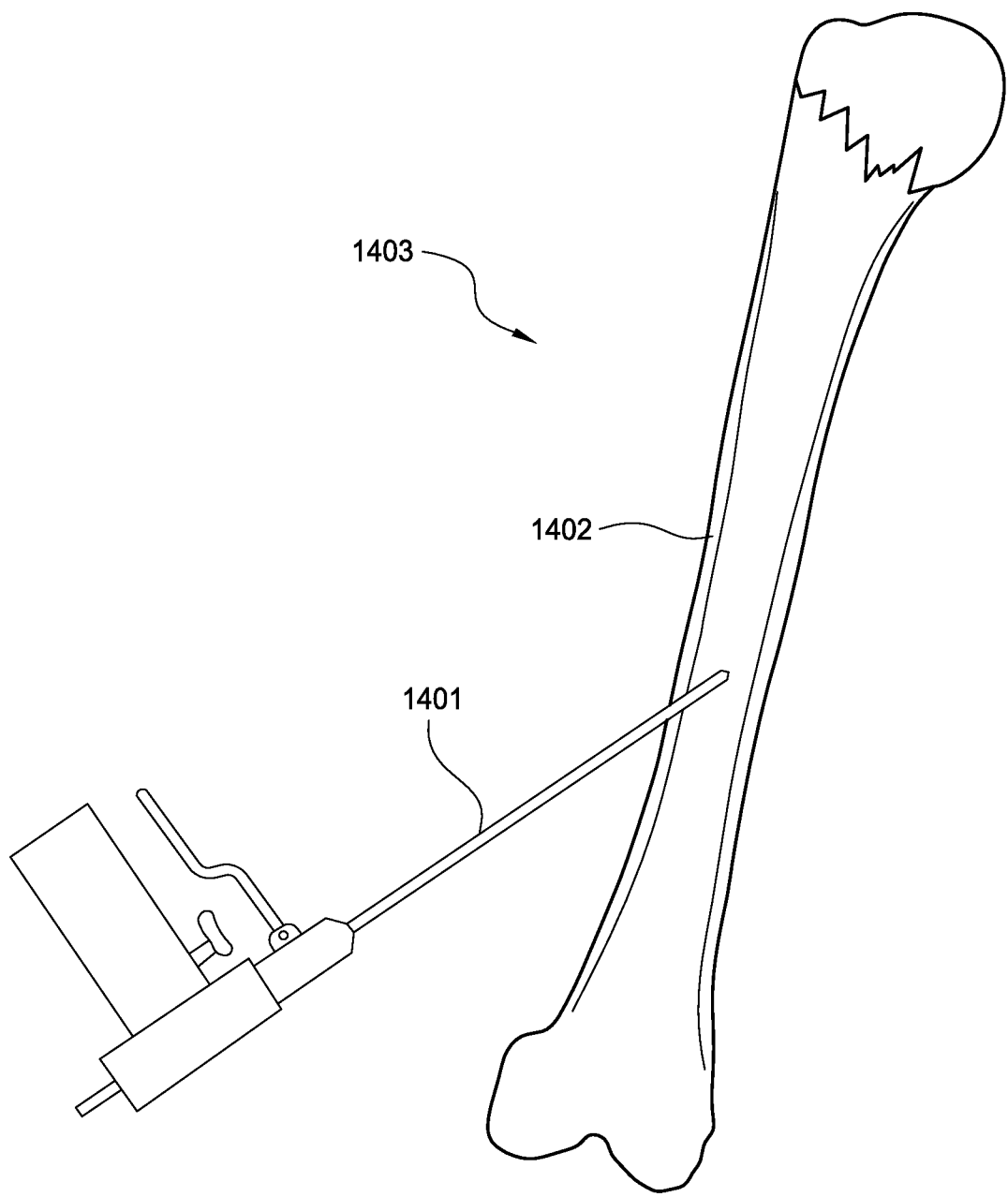
FIG. 14 illustrates the insertion of a guide wire into the cortex of a humerus, according to an embodiment of the invention.
Figure 15:
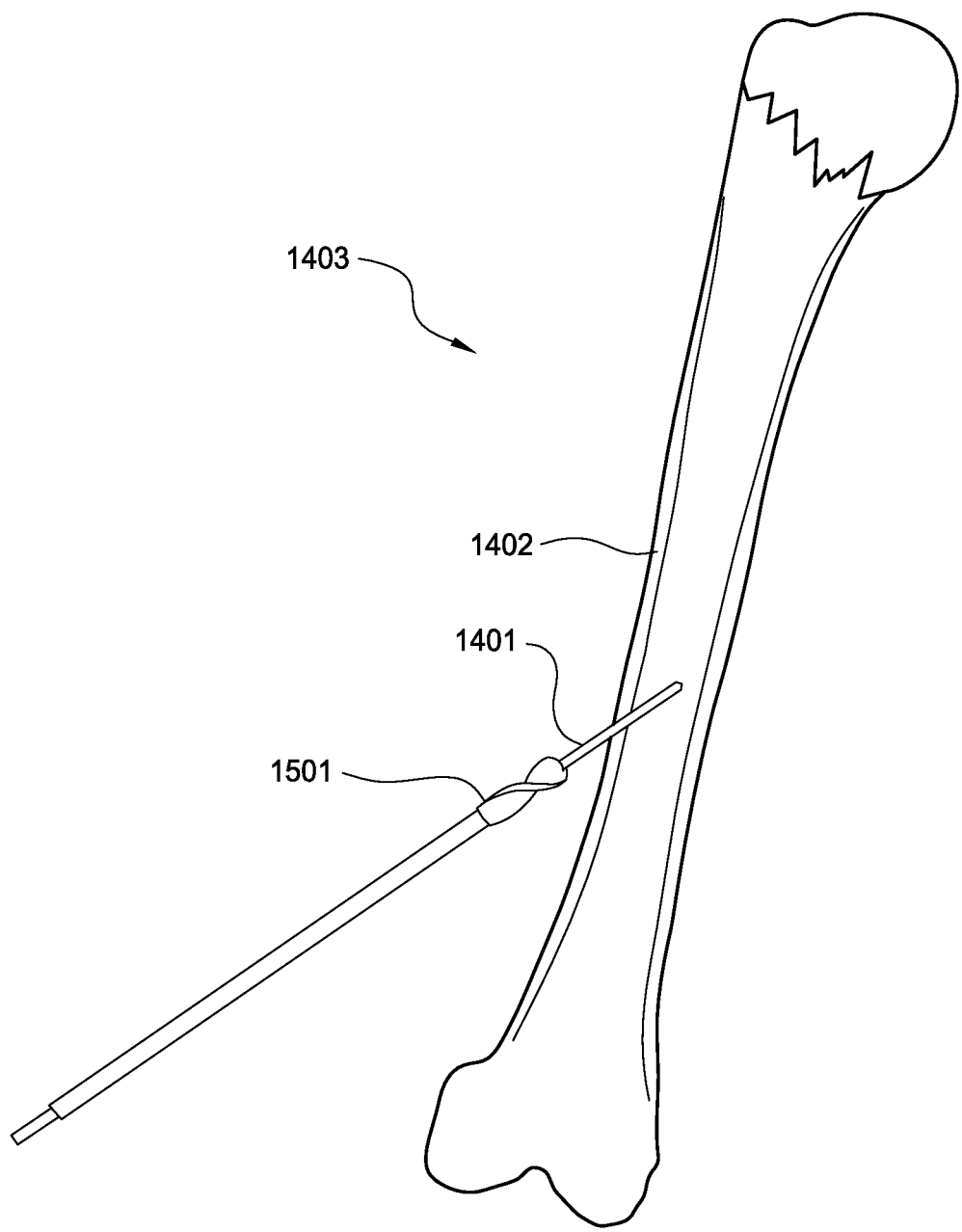
FIG. 15 illustrates a cannulated drill bit positioned around a guide wire immediately prior to drilling an opening into a cortex of a humerus, according to an embodiment of the invention.

In step 1301, an opening is formed in the cortex of a humerus bone at an oblique angle to expose the intramedullary cavity of the bone. The opening may be formed in a conventional manner, i.e., by drilling into the cortex at an oblique angle. Alternatively, a pointed guide wire may first be inserted into the cortex to guide the larger drill into the bone without slipping off the bone. FIG. 14 illustrates the insertion of a guide wire 1401 into the cortex 1402 of a humerus 1403, according to an embodiment of the invention. The opening is then formed in the cortex of the humerus using a cannulated drill bit that is positioned around the guide wire. In this way, the drill angle of entry into the cortex can be set without slippage off the bone and secondary injury to adjacent bone structures, thereby better facilitating the step of inserting the curved screw guide into the intramedullary cavity. FIG. 15 illustrates a cannulated drill bit 1501 positioned around guide wire 1401 immediately prior to drilling an opening into cortex 1402 of humerus 1403.

In step 1302, a flexible bone screw is inserted retrograde into a curved screw guide, where the flexible bone screw is substantially similar in organization and operation to flexible bone screw 300 in FIG. 3. Because of the retrograde insertion of the flexible bone screw into the curved screw guide, the shaft of the bone screw is contained in the curved screw guide and the threaded portion of the bone screw is positioned outside the curved screw guide at the insertion end thereof.

In step 1303, the curved screw guide and flexible bone screw are inserted into the intramedullary cavity of the fractured bone via the opening in the cortex. In step 1304, the flexible bone screw is oriented as desired by positioning the curved screw guide in the intramedullary cavity of the fractured bone. In step 1305, the flexible bone screw is rotated and advanced into the intramedullary cavity until the threaded portion of the flexible bone screw engages the subchondral bone of the humeral head. In step 1306, the curved screw guide is removed from the intramedullary cavity. The extra length of the screw shaft projecting from the bone and the surgical wound are then cut off, leaving enough to facilitate removal, according to standard surgical techniques. It is contemplated by the inventor that in certain cases, the dimensions and hardness of the bone and flexibility of the screw may allow insertion of the flexible bone screw without the aid of the curved screw guide.

While the foregoing is directed to embodiments of the present invention, other and further embodiments of the invention may be devised without departing from the basic scope thereof, and the scope thereof is determined by the claims that follow.

What is claimed is:

1. A method for repairing a bone fracture, comprising the steps of:
    drilling a hole through a cortex of the bone to expose an intramedullary cavity of the bone;
    inserting a flexible bone screw through the hole into the intramedullary cavity of the bone, the flexible bone screw having an elongated shaft and a threaded portion at a leading end thereof; and
    advancing the bone screw into the intramedullary cavity of the bone with associated elastic bending of the shaft, wherein the threaded portion has an outer diameter that is larger than a diameter of the shaft, and a ratio of the length of the threaded portion to a length of the flexible bone screw is about 0.2 or less and a ratio of the length of the flexible bone screw to a diameter of the shaft is at least 50, and
    wherein the shaft has a non-threaded surface between the threaded portion and a trailing end of the flexible bone screw.

2. The method according to claim 1, wherein the drilled hole is an oblique hole.

3. The method according to claim 1, wherein, with the associated elastic bending of the screw, the threaded tip is advanced within the intramedullary cavity of the bone in a direction that is approximately parallel to the bone axis.

4. The method according to claim 1, wherein, with the associated elastic bending of the screw, the threaded tip is advanced within the intramedullary cavity of the bone in a direction that approaches being parallel to the bone axis.

5. The method according to claim 1, wherein, with the associated elastic bending of the screw, the threaded tip is advanced within the intramedullary cavity of the bone in a direction that is more nearly parallel to the axis of the bone than is the shaft of the screw at the point where it passes through the hole in the bone cortex.

6. The method according to claim 1, further comprising the step of advancing the threaded tip across a bone fracture into a bony fragment.

7. The method according to claim 1, wherein the ratio of the length of the flexible bone screw to the diameter of the shaft is at least 100.

8. A method for repairing a bone fracture, comprising the steps of:
    drilling a hole through a cortex of the bone to expose an intramedullary cavity of the bone;
    inserting a flexible bone screw through the hole into the intramedullary cavity of the bone, the flexible bone screw having a tool engagement portion at a trailing end thereof, a threaded portion at a leading end thereof, and an elongated shaft between the trailing end and the leading end; and
    advancing the bone screw into the intramedullary cavity of the bone with associated elastic bending of the shaft, wherein a ratio of a length of the flexible bone screw to a diameter of the shaft is at least 50; the tool engagement portion has a diameter that is substantially the same or less than the diameter of the shaft; the threaded portion has an outer diameter that is larger than the diameter of the shaft; a ratio of the length of the threaded portion to the length of the flexible bone screw is about 0.2 or less; and a surface of the elongated shaft is substantially smooth.

9. The method according to claim 8, wherein a tip of the threaded portion has one of a spade point, a trocar point, and a corkscrew point.

10. The method according to claim 9, wherein the tip of the threaded portion has an included angle that is at least 80 degrees.

11. The method according to claim 8, wherein the threaded portion includes one or more cutting flutes.

12. The method according to claim 8, wherein the tool engagement portion has a rounded tip, is cylindrical, and has substantially the same diameter as the shaft.

13. The method according to claim 8, wherein the tool engagement portion comprises one of a portion with multiple flat sides, a recess portion, a threaded portion, an altered diameter portion whose diameter is less than the diameter of the shaft, and any combination of the foregoing.

14. The method according to claim 8, wherein the ratio of the length of the flexible bone screw to the diameter of the shaft is at least 100.

15. A method for repairing a bone fracture, comprising the steps of:
    inserting a flexible bone screw retrograde into a curved screw guide;
    inserting the curved screw guide having the flexible bone screw resting therein, into an intramedullary cavity of the bone;
    rotating the flexible bone screw to connect the flexible bone screw to a portion of the bone; and
    removing the curved screw guide from the intramedullary cavity after connecting the flexible bone screw to the portion of the bone.

16. The method according to claim 15, further comprising the step of positioning the flexible bone screw within the intramedullary cavity of the bone by moving the curved screw guide, prior to the step of rotating.

17. The method according to claim 15, wherein the bone comprises a humerus bone and the flexible bone screw is connected to a subchondral bone of the humerus bone.

18. The method according to claim 15, further comprising the step of drilling a hole through a cortex of the bone to expose the intramedullary cavity of the bone prior to the step of inserting the curved screw guide into the intramedullary cavity.

19. The method according to claim 18, wherein the step of drilling includes the steps of:
    drilling a wire through the cortex of the bone at an oblique angle; and
    drilling the hole through the cortex of the bone with a cannulated drill bit using the wire as a guide.

20. The method according to claim 15, wherein the curved screw guide has an inner diameter that is larger than a shaft diameter of the flexible bone screw, and an outer diameter of the curved screw guide is less than or equal to an outer diameter of a threaded portion of the flexible bone screw that is at a leading end of the flexible bone screw.

* * * * *